May 14, 1957 D. B. COLE Plant Pat. 1,600

HONEY LOCUST TREE

Filed Feb. 1, 1956

WITNESS

Addison E. Avery

INVENTOR

DAVID B. COLE

BY Oberlin & Limbach

ATTYS.

United States Patent Office

Plant Pat. 1,600
Patented May 14, 1957

1,600

HONEY LOCUST TREE

David B. Cole, Mentor Township, Ohio, assignor to The Cole Nursery Company, Painesville, Ohio, a corporation of Ohio Application February 1, 1956, Serial No. 562,909

1 Claim. (Cl. 47—59)

The present invention relates to a new and distinct variety of honey locust tree originated by me, having a novel habit of growth, and more particularly consists in a thornless honey locust tree, *Gleditsia triacanthos* L., Var. Inermis, having golden yellow foliage and a semi-dwarf habit of growth.

My new honey locust tree grows with a comparatively straight and strong stem and does not require staking. The clone is slow growing with short closely placed branches, producing a dwarf compact tree at maturity.

The color designations indicated below are taken from the "Horticultural Colour Chart" issued by The British Colour Council in collaboration with The Royal Horticultural Society, published 1938 by Henry Stone and Son, Ltd., Banbury, England.

The short branches are relatively uniformly spaced and arranged, and the branchlets are free of thorns. The bark color near the tips of the current year's growth of the young branchlets is Citron Green 763 shading progressively inwardly toward the stem through Scheeles Green 860/3, through Scheeles Green 860, and finally to Spinach Green o960/2. On their undersides, the color near the tips is Scheeles Green 860/3 shading progressively inwardly toward the stem through Scheeles Green 860 and finally to Spinach Green o960/2. Lenticels are produced very sparingly on the new growth.

The mature leaves are 14 to 18 cm. long and mostly bipinnate. The tendency is for the first leaves produced to be pinnate, and the others bipinnate. The bipinnate leaves have 8 to 14 pinnae, and the leaf rachis is hairy and slightly grooved, those exposed to the sun being faint Burnt Orange o14/2 to o14/1 on the upper side in late summer. The pinnate leaves have mostly 20 to 25 small oblong-lanceolate leaflets, 1.5 to 2.5 cm. long. The newly formed leaflets are Citron Green 763 progressing inwardly toward the stem as the foliage grows older through Citron Green 763/3, Fern Green o862/3, Fern Green o862, Spinach Green o960/3 to Spinach Green o960 which is the final color of the most mature inner leaves on both the upper and lower sides, the color holding well back on the season's growth. They are essentially glabrous or sparingly hairy on the midrib beneath, and the leaf margins are crenate-serrulate. The leaves are closely spaced, 2.5 to 4.0 cm. apart, lending to the compact appearance of the plant. The leaflets on the bipinnate leaves are of two sizes, 10–12 mm. and 18–22 mm. long; the two sizes often intermingle.

No flowers have yet been produced on this clone, consequently no records are available on the type of flowers borne, if any.

This new tree may be compared to the honey locust tree of Plant Patent 1313, being generally similar in the color of its foliage. The principal contrasting feature is the much more slow and compact habit of growth of the present tree, providing a straight but dwarf and compact plant in which the golden leaflet color persists for a somewhat longer period toward the center of the plant. The young growing branchlets have a wax-like sheen. The color of the trunk bark on young trees about five to eleven years old is approximately Willow Green ooo862/2.

I have propagated my new thornless honey locust tree at Painesville, Ohio, asexually by budding, and the tree can be very readily propagated in this manner, perpetuating all of its original character. The original parent specimen was a seedling grown by me at the same location. Such original parent specimen was discovered by me in a plantation of approximately 10,000 thornless money locust seedlings grown by me from seed from selected parent trees exhibiting some tendency toward the desired characteristics.

In view of its very attractive color and dwarf form, my new honey locust tree is particularly well adapted for use in landscape gardening of both formal and informal character. In common with other honey locusts, it is, of course, relatively immune to disease and insect pests.

Referring now more particularly to the drawing.

Figures 1, 2, 3:
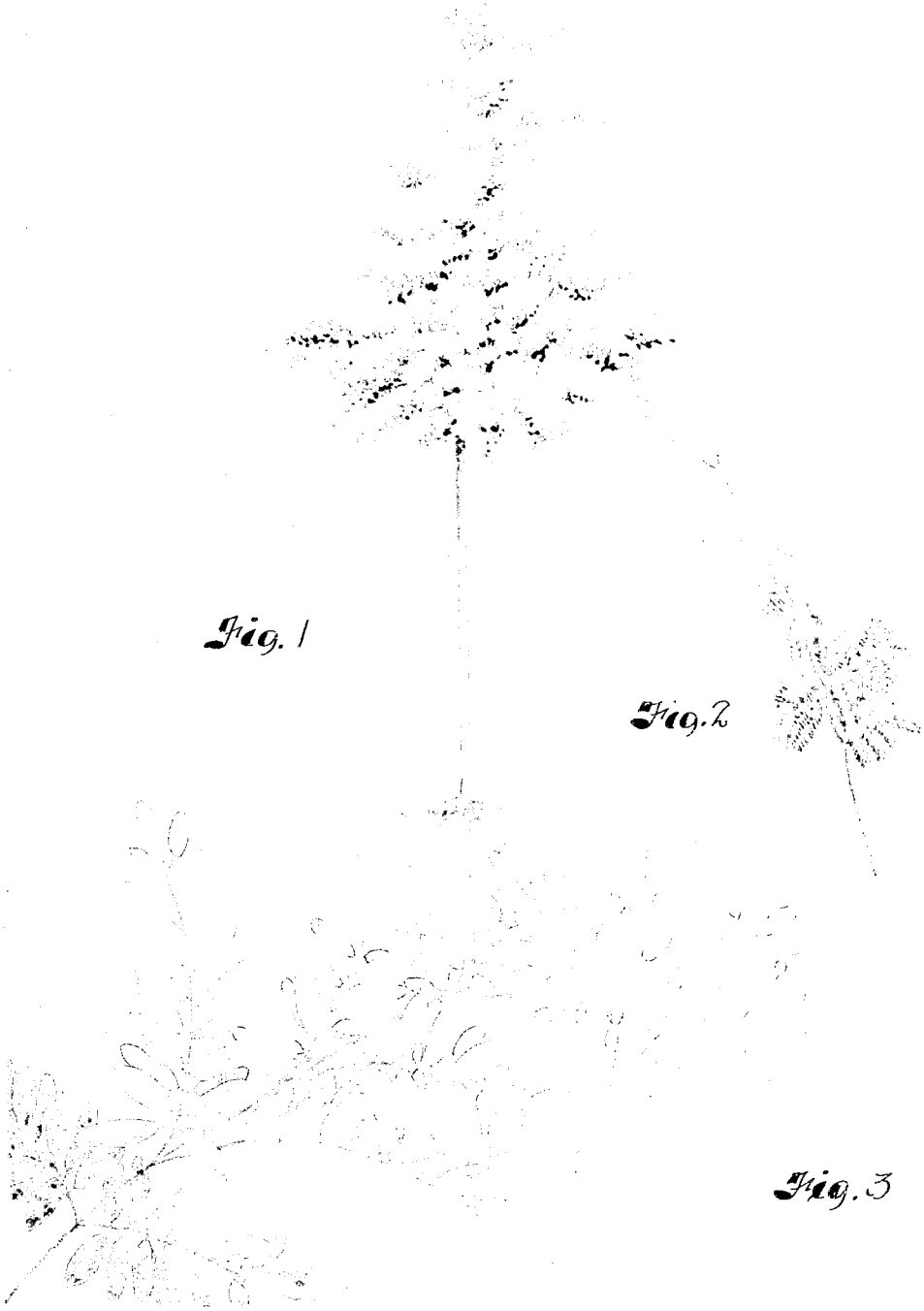
Fig. 1 shows a specimen of my new thornless honey locust tree several years of age toward the end of the normal growing season.
Fig. 2 shows an individual branch.
Fig. 3 shows a leaf with leaflets of different ages.

I claim:

A new and distinct variety of thornless honey locust tree, *Gleditsia triacanthos* L., Var. Inermis, having an unusually straight trunk, uniformly distributed well-spaced branches, unusually dense foliage of a golden yellow color similar to that of the honey locust tree of Plant Patent 1313, particularly characterized in that the rate of growth is very much less than that of the tree of Patent 1313 producing a relatively compact dwarf specimen.

No references cited.